United States Patent [19]

Sehring et al.

[11] 4,364,875
[45] Dec. 21, 1982

[54] PROCESS FOR THE PREPARATION OF CERTAIN DIPHENYL ETHERS

[75] Inventors: Richard Sehring; Wolfgang Buck, both of Ingelheim am Rhein, Fed. Rep. of Germany

[73] Assignee: Celamerck GmbH & Co. KG, Ingelheim am Rhein, Fed. Rep. of Germany

[21] Appl. No.: 281,123

[22] Filed: Jul. 7, 1981

Related U.S. Application Data

[63] Continuation of Ser. No. 188,480, Sep. 18, 1980, abandoned.

[30] Foreign Application Priority Data

Sep. 24, 1979 [DE] Fed. Rep. of Germany ....... 3938595

[51] Int. Cl.³ .................... C07C 121/78; C07C 95/08; C07C 101/44; C07C 109/04
[52] U.S. Cl. .................................. 260/465 E; 560/9; 560/21; 562/426; 562/435; 564/166; 564/310; 564/399; 564/430
[58] Field of Search .................... 260/465 E; 564/399, 564/430, 166, 310; 71/105, 121; 560/9, 21; 562/426, 435

[56] References Cited

U.S. PATENT DOCUMENTS

| | | | |
|---|---|---|---|
| 3,798,276 | 3/1974 | Bayer et al. | 71/105 X |
| 3,914,310 | 10/1975 | Frick et al. | 564/430 |
| 3,920,445 | 11/1975 | Wagner et al. | 71/105 |
| 3,920,739 | 11/1975 | Suda et al. | 564/399 X |
| 4,039,588 | 8/1977 | Wilson et al. | 71/121 X |

*Primary Examiner*—Dolph H. Torrence
*Attorney, Agent, or Firm*—Hammond & Littell, Weissenberger & Muserlian

[57] ABSTRACT

The method of preparing a compound of the formula

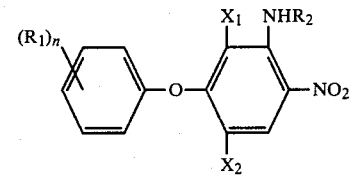

wherein
$R_1$ is hydrogen, halogen, alkyl of 1 to 8 carbon atoms, trifluoromethyl or acetyl;
n is 1 when $R_1$ has all the defined meanings, or 2 or 3 when $R_1$ is halogen or alkyl;
$R_2$ is hydrogen; alkyl of 1 to 16 carbon atoms; alkenyl of 2 to 16 carbon atoms; alkinyl of 2 to 16 carbon atoms; monosubstituted alkyl of 2 to 6 carbon atoms, where the substituent is hydroxyl, alkoxy of 1 to 4 carbon atoms, phenoxy, halo-phenoxy, (alkyl of 1 to 4 carbon atoms) phenoxy, (alkoxy of 1 to 4 carbon atoms)phenoxy, nitro-phenoxy, cyano-phenoxy, amino or (alkyl of 1 to 4 carbon atoms)thio; benzyl; halo-benzyl; —$NR_3R_4$; —$CHR_3$—$COOR_4$; or —$CHR_3$—$CONR_4R_5$, where $R_3$, $R_4$ and $R_5$ are each hydrogen or alkyl of 1 to 8 carbon atoms; and
$X_1$ and $X_2$ are each hydrogen or halogen,
which comprises reacting a compound of the formula

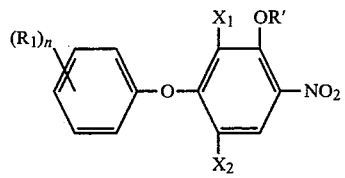

wherein
n, $R_1$, $X_1$ and $X_2$ have the meanings previously defined, and
$R_1$ is unsubstituted or substituted phenyl, with an amine of the formula $H_2N$—$R_2$ wherein $R_2$ has the meanings previously defined, at a temperature between about 20° and 160° C.

2 Claims, No Drawings

PROCESS FOR THE PREPARATION OF CERTAIN DIPHENYL ETHERS

This is a continuation of copending application Ser. No. 188,480, filed Sept. 18, 1980, now abandoned.

This invention relates to a novel process for the preparation of certain substituted diphenyl ethers.

More particularly, the present invention relates to a novel process for the preparation of diphenyl ethers of the formula

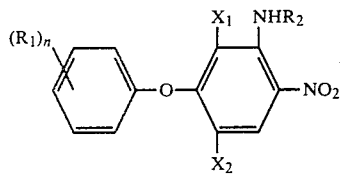

wherein
- $R_1$ is hydrogen, halogen, alkyl of 1 to 8 carbon atoms, trifluoromethyl, CN, acetyl; $C_1$–$C_4$-alkoxy or
- n is 1 when $R_1$ has all the defined meanings, or 2 or 3 when $R_1$ is halogen or alkyl;
- $R_2$ is hydrogen; alkyl of 1 to 18 carbon atoms; alkenyl of 2 to 16 carbon atoms; alkinyl of 2 to 16 carbon atoms; monosubstituted alkyl of 2 to 6 carbon atoms, where the substituent is hydroxyl, alkoxy of 1 to 4 carbon atoms, phenoxy, halo-phenoxy, (alkyl of 1 to 4 carbon atoms) phenoxy, (alkoxy of 1 to 4 carbon atoms)phenoxy, nitro-phenoxy, cyano-phenoxy, amino or (alkyl of 1 to 4 carbon atoms)thio; benzyl; halo-benzyl; trifluoromethyl-benzyl; —$NR_3R_4$; —$CHR_3$—$COOR_4$; or —$CHR_3$—$CONR_4R_5$, where
- $R_3$, $R_4$ and $R_5$, which may be identical to or different from each other, are each hydrogen or alkyl of 1 to 8 carbon atoms; and
- $X_1$ and $X_2$, which may be identical to or different from each other, are each hydrogen or halogen.

The term "halogen" includes fluorine, chlorine, bromine and iodine. Preferred embodiments of halogen are fluorine, chlorine and bromine, with fluorine and chlorine being especially preferred. To the extent that $R_1$, $R_2$, $R_3$, $R_4$ and $R_5$ represent or contain hydrocarbon groups, these may be straight or branched.

Preferred embodiments of $R_1$ through $R_5$ are the following:
- $R_1$—hydrogen, fluorine, chlrorine, bromine or methyl;
- $R_2$—hydrogen, alkyl of 1 to 4 carbon atoms, allyl, β-hydroxy-ethyl, 4-fluoro-benzyl, 4-chloro-benzyl or dimethylamino;
- $R_3$—hydrogen or methyl;
- $R_4$ and $R_5$—alkyl of 1 to 4 carbon atoms; and
- $X_1$ and $X_2$—chlorine and hydrogen, respectively; chlorine and bromine, respectively; or bromine and chlorine, respectively.

When n is 2 or 3, the $R_1$ substituents may be identical to or different from each other.

THE PRIOR ART

Some of the compounds embraced by formula I are disclosed in German Offenlegungsschrift No. 2,831,262, namely those of the formula

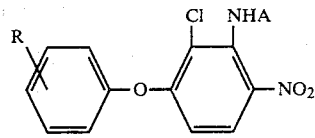

wherein
- A is hydrogen, straight alkyl of 1 to 6 carbon atoms, cycloalkyl of 3 to 6 carbon atoms, chloro(alkyl of 2 to 6 carbon atoms), hydroxy(alkyl of 2 to 6 carbon atoms) or allyl; and
- R is hydrogen, fluorine, bromine, chlorine, trifluoromethyl, methyl or methoxy.

These compounds are very effective herbicides. They are prepared by reacting a phenolate with a halogenated nitroaniline in the presence of a solvent such as acetonitrile, dimethylformamide and dimethylsulfoxide. The nitroaniline must be free from isomers and diamines. Moreover, N-substituted nitroanilines easily undergo side-reactions and thus reduce the yields.

OBJECTS OF THE INVENTION

It is an object of the present invention to provide a novel process for the preparation of diphenyl ethers of the formula I which avoids the use of nitroanilines and thus leads to very good yields of virtually isomer-free end products.

Another object of the present invention is to provide novel herbicidal diphenyl ethers.

Still other objects and advantages of the invention will become apparent as the description thereof proceeds.

DESCRIPTION OF THE INVENTION

We have discovered that the above objects are achieved by reacting a compound of the formula

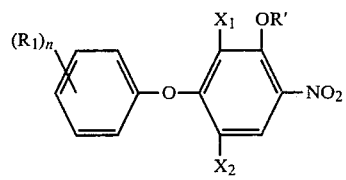

wherein
- n, $R_1$, $X_1$ and $X_2$ have the same meanings as in formula I, and
- R' is unsubstituted or substituted phenyl, with an amine of the formula

wherein $R_2$ has the same meanings as in formula I, at a temperature between about 20° and 160° C.

The radical R' in formula II is generally of the formula

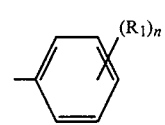

wherein $R_1$ and n have the meanings previously defined, but it may also represent other substituted phenyl radicals because, whatever substituents might be attached to the phenyl ring, they have no significant influence on the reaction to the extent that they are sufficiently stable under the reaction conditions.

The reaction may be performed in an inert organic solvent medium such as dioxane, tetrahydrofuran, benzene, toluene, xylene, a chlorinated hydrocarbon or dimethyl sulfoxide, or also in water. The choice of the solvent medium is not critical, but it is preferred to use a solvent in which the reactants are sufficiently soluble.

Compared to the process described in German Offenlegungsschrift No. 2,831,261, the novel process of the present invention has the advantage that the starting compounds of the formula II of suitable quality are easier to prepare than the chloronitroanilines required for the prior art process, that it consistently produces very good yields, and that it may be carried out with inexpensive solvents such as water.

Some of the starting compounds of the formula II are known. However, the compounds of the formula II may also be prepared by a novel method, namely by reacting a compound of the formula

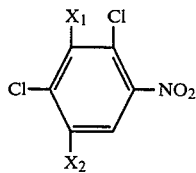

(V)

wherein $X_1$ and $X_2$ have the meanings previously defined, such as 2,3,4-trichloro-nitrobenzene or 2,3,4,5-tetrachloronitrobenzene, with a phenolate of the formula

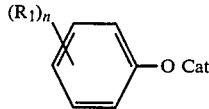

(VI)

wherein $R_1$ and n have the meanings previously defined, and Cat is 1 equivalent of a cation.

The reaction is preferably performed with an alkali metal phenolate of the formula VI, especially with sodium phenolate, or with a mixture of the particular phenol and an alkali metal carbonate. If a single phenol is used, especially unsubstituted phenol, the phenol reactant may at the same time serve as the solvent medium for the reaction. However, the use of dimethylsulfoxide as the solvent is especially advantageous.

The two chlorine atoms in the 2- and 4-positions of the compounds of the formula V, which are exchanged for phenoxy groups, exhibit distinctly different reactivities. Therefore, it is possible to synthesize compounds of the formula II with two different phenoxy groups in the 2- and 4-position with respect to the nitro substituent. For this purpose, the chlorine atoms adjacent to the nitro group in a compound of the formula V is first exchanged for the desired phenoxy radical under mild conditions, and then the chlorine atom in the 4-position is exchanged for the other desired phenoxy radical under more severe conditions.

As indicated above, the process of the present invention can be used to prepare compounds of the formula I which embraces known as well as heretofore unknown compounds. The novel compounds are those of the formula I not embraced by formula Ia. The novel compounds also exhibit very effective herbicidal properties; in addition, they are useful as intermediates for the preparation of novel pesticidal agents or novel drugs, since their functional groups make a multitude of modifications possible.

The following examples illustrate the present invention and will enable others skilled in the art to understand it more completely. It should be understood, however, that the invention is not limited solely to the particular examples given below.

I. Preparation of starting compounds

EXAMPLE A

2-Chloro-4-nitro-1,3-diphenoxy-benzene (a) A mixture of 114.5 gm of 2,3,4-trichloronitrobenzene, 400 ml of dimethylsulfoxide and 130 gm of sodium phenolate was stirred for 1 hour at 100° C. Thereafter, the reaction mixture was admixed with water and then extracted with chloroform. The chloroform extract was washed with dilute sodium hydroxide, dried with sodium sulfate, the chloroform was evaporated, and the residue was recrystallized from ethanol. 152 gm (89% of theory) of the compound named in the heading, m.p. 106°–107° C., were obtained.

(b) A mixture of 56.7 gm (0.25 mol) of 2,3,4-trichloronitrobenzene and 34.5 gm (0.25 mol) of potassium carbonate was heated for 1 hour at 130°–140° C. Thereafter, the reaction mixture was added to 2 N sodium hydroxide, and the mixture was washed up as described in (a) above. More than 95% of theory of the title compound, m.p. 106°–107° C., was obtained.

EXAMPLE B

6-Chloro-4-nitro-1,3-diphenoxy-benzene

A mixture of 1 mol of 2,4,5-trichloro-1-nitrobenzene, 2 mols of potassium phenolate and phenol was heated for 1 hour at 165° C., and the reaction product was isolated as described in Example A(a), yielding the title compound, m.p. 95° C. (recrystallized from ethanol).

EXAMPLE C 2,6-Dichloro-4-nitro-1,3-diphenoxy-benzene (a) A mixture of 26.2 gm (0.1 mol) of 2,3,4,5-tetrachloro-1-nitro-benzene, 20.7 gm of phenol, 30 gm of potassium carbonate and 100 ml of dimethylsulfoxide was heated for 4 hours at 110° C. Thereafter, the reaction mixture was added to water, and the precipitated product was collected by suction filtration. 33.5 gm (89% of theory) of the title compound, m.p. 152° C. (recrystallized from ethyl acetate) were obtained.

(b) A mixture of 52.4 gm of 2,3,4,5-tetrachloro-1-nitro-benzene, 122 gm of phenol and 60 gm of potassium carbonate was heated for 1½ hours at 160° C. Thereafter, the still hot reaction mixture was stirred into 1.2 liters of 2 N sodium hydroxide, and the precipitated product was collected by suction filtration and recrystallized from 300 ml of ethyl acetate. 70.5 gm (93.8% of theory) of the title compound, m.p. 164° C., were obtained.

EXAMPLE D

2-Chloro-4-nitro-5-phenoxy-1-(2,4,5-trichloro-phenoxy)benzene

A mixture of 28.4 gm of 4,5-dichloro-2-nitro-1-phenoxy-benzene, 21.6 gm of 2,4,5-trichloro-phenol, 10 ml of 10 N sodium hydroxide and 80 ml of dimethylsulfoxide was stirred for 6 hours at 150° C. and then allowed to stand overnight at room temperature. Thereafter, the reaction mixture was stirred into 600 ml of water, the aqueous mixture was made alkaline, and the precipitated reaction product was taken up in chloroform. The organic phase was washed with water, dried and evaporated, and the residue was recrystallized from 200 ml of ethanol, yielding 43 gm (97% of theory) of the light yellow crystalline title compound, m.p. 84° C.

EXAMPLE E

2-Chloro-4-nitro-5-phenoxy-1-(2,5-dichloro-4-bromo-phenoxy)-benzene

A mixture of 28.4 gm of 4,5-dichloro-2-nitro-1-phenoxy-benzene, 24.2 gm of 2,5-dichloro-4-bromophenol, 10 ml of 10 N sodium hydroxide and 80 ml of dimethylsulfoxide was stirred for 5 hours at 100° C. Thereafter, the reaction mixture was stirred into 700 ml of 1 N sodium hydroxide, the mixture was allowed to stand overnight at room temperature, the liquid phase was decanted, and the precipitated product was taken up in chloroform. The chloroform solution was washed with water, dried with sodium sulfate and evaporated, and the residue was recrystallized from a mixture of 200 ml ethanol and 2 ml dimethylformamide. 36.5 gm (75% of theory) of the light yellow crystalline title compound, m.p. 85° C., were obtained.

EXAMPLE F

2-Chloro-4-nitro-3-phenoxy-1-(2,5-dichloro-4-methyl-thiophenoxy)-benzene

A mixture of 14.2 gm of 2,3-dichloro-6-nitro-1-phenoxy-benzene, 10.2 gm of 2,5-dichloro-4-methylthiophenol, 5.0 ml of 10 N sodium hydroxide and 40 ml of dimethylsulfoxide was stirred for 5 hours at 100° C. and then allowed to stand overnight at room temperature. Thereafter, the reaction mixture was admixed with 400 ml of 1 N sodium hydroxide, and the product precipitated thereby was collected and recrystallized from 150 ml of ethanol. 20.5 gm (90% of theory) of the light yellow crystalline title compound, m.p. 138°-144° C., were obtained.

EXAMPLE G

2-Chloro-4-nitro-3-phenoxy-1-(2,4,5-trichloro-phenoxy)benzene

A mixture of 28.4 gm of 2,3-dichloro-6-nitro-1-phenoxy-benzene, 21.6 gm of 2,4,5-trichloro-phenol, 10 ml of 10 N sodium hydroxide and 80 ml of dimethylsulfoxide was stirred for 6 hours at 100° C. Thereafter, the reaction mixture was admixed with 600 ml of 1 N sodium hydroxide, and the precipitated product was collected by suction filtration and recrystallized from 150 ml of ethanol. 31 gm (77.4% of theory) of the title compound, m.p. 112° C., were obtained. An additional amount of the product (about 6 gm) was obtained by evaporating the filtrate.

EXAMPLE H

2-Chloro-4-nitro-3-phenoxy-1-(4-cyano-phenoxy)-benzene

A mixture of 14.2 gm of 2,3-dichloro-6-nitro-1-phenoxy-benzene, 6.5 gm of 4-cyano-phenol, 40 ml of dimethylsulfoxide and 50 ml of 10 N sodium hydroxide was stirred for 3 hours at 100° C. Thereafter, the reaction mixture was diluted with water, the aqueous mixture was extracted with chloroform, the organic extract solution was dried, and the chloroform was distilled off.

The residue was purified by passing it through a silica-gel column and recrystallizing it from ethanol, yielding 11 gm (60.2% of theory) of the colorless crystalline title compound, m.p. 140°-142° C.

II. Preparation of End Products

EXAMPLE 1

2-Chloro-3-phenoxy-6-nitro-N-[1-(methyl-carbamoyl)-ethyl]-aniline

A mixture of 63.3 gm of 2-chloro-4-nitro-1,3-diphenoxy-benzene, 200 ml of dioxane and 60 mg of α-alanine-N-methylamide was stirred for 24 hours at 70° C. Thereafter, the dioxane was distilled off, the residue was dissolved in ethylene chloride, and the resulting solution was extracted with dilute sodium hydroxide. The organic phase was dried with sodium sulfate, the solvent was distilled off, and the residue was recrystallized from ethanol, yielding 61.5 gm (87.2% of theory) of the compound of the formula

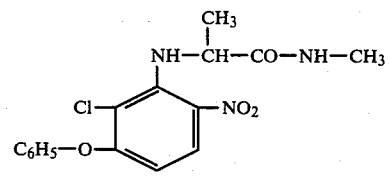

which had a melting point of 122° C. The product was thin-layer chromatographically uniform.

| Analysis: | C | H | Cl |
|---|---|---|---|
| Calculated: | 54.62% | 4.55% | 10.10% |
| Found: | 54.30% | 4.41% | 10.07% . |

EXAMPLE 2

2-Chloro-3-phenoxy-6-nitro-N-[2-(2,5-dichloro-phenoxy)-ethyl]-aniline

The procedure described in Example 1 was repeated, except that the alanine-N-methylamide was replaced by [2-(2,5-dichloro-phenoxy)-ethyl]-amine. The reaction product was a thin-layer chromatographically uniform oil which was obtained with a yield of 97% of theory.

| Analysis: | C | H | Cl |
|---|---|---|---|
| Calculated: | 52.92% | 3.31% | 23.46% |
| Found: | 52.87% | 3.24% | 23.70% . |

EXAMPLE 3

4-Chloro-3-phenoxy-6-nitro-N-allyl-aniline

A mixture of 63.3 gm of 6-chloro-4-nitro-1,3-diphenoxy-benzene, 120 ml of dioxane and allylamine in substantial excess over the stoichiometrically required amount was heated for 12 hours at 60° C. Thereafter, the dioxane was distilled off, the residue was dissolved in methylene chloride, the resulting solution was washed with dilute sodium hydroxide, the organic phase was dried with sodium sulfate, and the methylene chloride was distilled off. The residue was recrystallized from a mixture of toluene and hexane and further purified on a silicagel column, yielding 51 gm (83.6% of theory) of the title compound, m.p. 81°–82° C.

| Analysis:   | C      | H     | Cl      |
|-------------|--------|-------|---------|
| Calculated: | 59.11% | 4.27% | 11.66%  |
| Found:      | 58.90% | 4.32% | 11.80%. |

EXAMPLE 4

4-Chloro-3-phenoxy-6-nitro-N-(2-amino-ethyl)-aniline hydrochloride 6.83 gm of 6-chloro-4-nitro-1,3-diphenoxy-benzene were dissolved in 15 ml of dioxane, an excess of 1,2-diamino-ethane was added to the solution, and the mixture was heated for 12 hours at 70° C. Thereafter, the reaction mixture was worked up as in Example 3, and the reaction product was purified by recrystallization from ethanol. 6.1 gm (88% of theory) of the white crystalline compound of the formula

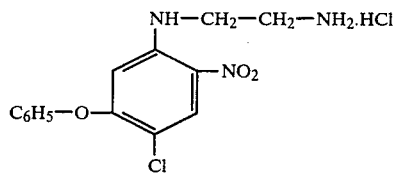

having a melting point of 255° C. (decomp.) were obtained.

EXAMPLE 5

3-Phenoxy-6-nitro-N-allyl-aniline

A mixture of 10 gm of 4-nitro-1,3-diphenoxy-benzene, 30 ml of tetrahydrofuran and 10 ml of allylamine was refluxed for 8 hours. Thereafter, the reaction mixture was worked up as in Example 3, and the reaction product was recrystallized from ethanol, yielding 6.1 gm (69% of theory) of the thin-layer chromatographically (cyclohexane/toluene=1:1) uniform title compound, m.p. 67°–68° C.

| Analysis:   | C      | H     | N       |
|-------------|--------|-------|---------|
| Calculated: | 66.67% | 5.19% | 10.37%  |
| Found:      | 66.85% | 5.30% | 10.24%. |

EXAMPLE 6

2-Chloro-3-phenoxy-6-nitro-aniline (a) 68.3 gm of 2-chloro-4-nitro-1,3-diphenoxy-benzene were dissolved in 300 ml of toluene, and the solution was admixed with 100 ml of concentrated aqueous ammonia in an autoclave. The autoclave was then closed, the internal pressure was increased to 3 bar with gaseous ammonia, and the contents were heated for 12 hours at 120° C., whereby the internal pressure rose to about 13 bar. Thereafter, the contents were allowed to cool, and the organic phase was separated, extracted with dilute hydrochloric acid, dried with sodium sulfate and the toluene was distilled off. The reaction product was obtained with virtually quantitative yield (54 gm). Gas-chromatographic analysis revealed that the reaction product contained 98% of the title compound, m.p. 81°–82° C.

(b) The procedure described in (a) was repeated, except that no gaseous ammonia was introduced into the autoclave and the contents were heated at 150° C. The yield of reaction product was virtually quantitative. According to gas-chromatographic analysis, the reaction product consisted of 96% title compound and about 4% of starting material.

EXAMPLE 7

2-Chloro-3-(2,5-dichloro-4-methylthio-phenoxy)-6-nitro-N-benzyl-aniline

A mixture of 4.6 gm of 2-chloro-4-nitro-3-phenoxy-1-(2,5-dichloro-4-methylthio-phenoxy)-benzene, 3.0 gm of benzylamine and 10 ml of dioxane was stirred for 6 hours at 40° C. Thereafter, the reaction mixture was allowed to stand overnight and was then evaporated. The residue was taken up in chloroform, and the resulting solution was extracted first with dilute sodium hydroxide and then with water, dried with sodium sulfate and evaporated. The dark brown oil left behind was purified on a silicagel column, yielding 4.2 gm of the thin-layer chromatographically uniform title compound in the form of an orange, viscous oil.

EXAMPLE 8

4-Chloro-3-(2,5-dichloro-4-bromo-phenoxy)-6-nitro-N-allyl-aniline

A mixture of 4.9 gm of 2-chloro-4-nitro-5-phenoxy-1-(2,5-dichloro-4-bromo-phenoxy)-benzene, 1.8 gm of allylamine and 10 ml of dioxane was stirred first for 7 hours at 40° C. and then for 3 hours at 60° C. Thereafter, the reaction solution was evaporated, the residue was taken up in chloroform, and the resulting solution was washed first with an acid solution and then with an alkaline solution, dried with sodium sulfate and evaporated. The raw reaction product thus obtained (5.6 gm) was purified on a silicagel column, yielding 3.0 gm (66.6% of theory) of the yellow crystalline title compound, m.p. 102.5° C.

EXAMPLE 9

4-Chloro-3-(2,5-dichloro-4-bromo-phenoxy)-6-nitro-N-benzyl-aniline

A mixture of 4.9 gm of 2-chloro-4-nitro-5-phenxoy-1-(2,5-dichloro-4-bromo-phenoxy)-benzene, 3.0 gm of benzylamine and 10 ml of dioxane was reacted and worked up and described in Example 8. The raw reaction product (6.2 gm) was stirred with 30 ml of hot ethanol, and after cooling to room temperature the solid phase was suction-filtered off, yielding 3.2 gm of the dark yellow crystalline title compound, m.p. 157° C.

EXAMPLE 10

2-Chloro-3-(2,5-dichloro-4-methylthio-phenoxy)-6-nitro-N-allyl-aniline

A mixture of 4.6 gm of 2-chloro-4-nitro-3-phenoxy-1-(2,5-dichloro-4-methylthio-phenoxy)-benzene, 1.8 gm of allylamine and 10 ml of dioxane was stirred for 6 hours at 40° C. and was then allowed to stand overnight at room temperature. Thereafter, the reaction mixture was evaporated, the residue was taken up in chloroform, and the resulting solution was washed first with an acid solution and then with an alkaline solution, dried with sodium sulfate and evaporated. The raw product thus obtained (5.2 gm) was recrystallized from 20 ml of ethanol, yielding 3.8 gm (91% of theory) of the orange crystalline compound, m.p. 107° C., of the formula

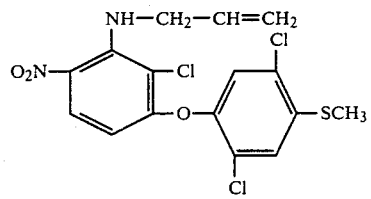

EXAMPLE 11

2-Chloro-3-phenoxy-6-nitro-N-(4-chloro-benzyl)-aniline

A mixture of 5 gm of 2-chloro-4-nitro-1,3-diphenoxy-benzene, 10 ml of dioxane and 6 gm of 4-chlorobenzylamine was stirred for 12 hours at 80° C. Thereafter, the reaction mixture was evaporated, the residue was taken up in chloroform, the resulting solution was extracted with 1 N sodium hydroxide, and the organic phase was dried with sodium sulfate. The chloroform was distilled off, and the residue was recrystallized from ethanol, yielding 4.7 gm (82.7% of theory) of the title compound, m.p. 95°–96° C.

Using an analogous procedure, but substituting 4-fluoro-benzylamine for 4-chloro-benzylamine, yellow crystalline 2-chloro-3-phenoxy-6-nitro-N-(4-fluoro-benzyl)-aniline, m.p. 75°–76° C., was obtained with a yield of 4.1 gm (75.4% of theory).

EXAMPLE 12

2-Chloro-3-phenoxy-6-nitro-N-(3-trifluoromethyl-benzyl)-aniline

A mixture of 3.41 gm of 2-chloro-4-nitro-1,3-diphenoxy-benzene, 5 ml of dioxane and 4 gm of 3-trifluoromethyl-benzylamine was stirred for 12 hours at 100° C. Thereafter, the reaction mixture was evaporated, the residue was taken up in chloroform, the resulting solution was extracted first with 2 N sodium hydroxide and then with 2 N hydrochloric acid, and the organic phase was dried with sodium sulfate. The chloroform was distilled off, leaving 4.0 gm (95% of theory) of the title compound as a viscous yellow oil.

| Analysis: | C | H | N |
|---|---|---|---|
| Calculated: | 56.8% | 3.32% | 6.64% |
| Found: | 56.5% | 3.57% | 6.47% |

EXAMPLE 13

4-Chloro-3-phenoxy-6-nitro-N-(3-trifluoromethyl-benzyl)-aniline

Using a procedure analogous to that described in Example 12, 3 gm (71.2% of theory) of the title compound, m.p. 140°–142° C. (recrystallized from ethanol), were obtained by stirring a mixture of 3.51 gm of 6-chloro-4-nitro-1,3-diphenoxy-benzene, 4 gm of 3-trifluoromethyl-benzylamine and 5 ml of dioxane for 20 hours at 100° C.

EXAMPLE 14

2-Chloro-3-(4-cyano-phenoxy)-6-nitro-N-allyl-aniline

A mixture of 4 gm of 2-chloro-4-nitro-3-phenoxy-1-(4-cyano-phenoxy)-benzene, 10 ml of dioxane and 2 gm of allylamine was allowed to stand at room temperature for 30 hours. Thereafter, the dioxane was distilled off, the residue was taken up in chloroform, the resulting solution was extracted with dilute sodium hydroxide, the organic phase was dried with sodium sulfate, the chloroform was distilled off, and the residue was recrystallized from ethanol. 3.5 gm (97.2% of theory) of the yellow crystalline title compound, m.p. 85°–87° C., were obtained.

EXAMPLE 15

2-Chloro-3-phenoxy-6-nitro-N',N'-dimethyl-hydrazine

A mixture of 6.85 gm of 2-chloro-4-nitro-1,3-diphenoxy-benzene, 20 ml of dioxane and 9 gm of N,N-dimethylhydrazine was refluxed for 10 hours. Thereafter, the dioxane was distilled off, the residue was taken up in chloroform, and the resulting solution was washed with dilute sodium hydroxide and dried with sodium sulfate. The chloroform was distilled off, the residue was dissolved in diethyl ether, gaseous hydrogen chloride was passed through the solution, and the precipitate formed thereby was collected by suction filtration. The filter cake was stirred with water, the aqueous mixture was extracted with chloroform, the organic phase was dried with sodium sulfate, and the chloroform was distilled off, leaving 4.5 gm (73% of theory) of the formula

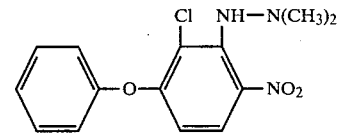

as an orange oil.

| Analysis: | C | H | N |
|---|---|---|---|
| Calculated: | 54.7% | 4.55% | 13.65% |
| Found: | 55.11% | 4.86% | 13.36% |

EXAMPLE 16

2-Chloro-3-phenoxy-6-nitro-N-(6-amino-hexyl)-aniline

A mixture of 17.5 gm of 2-chloro-4-nitro-1,3-diphenoxy-benzene, 30 ml of dioxane and 9 gm of 1,6-diaminohexane was stirred for 4 hours at 50° C. Thereafter, the dioxane was distilled off, the residue was taken up in chloroform, the resulting solution was washed first with dilute sodium hydroxide and then with dilute hydrochloric acid, dried with sodium sulfate, and the chloroform was distilled off. The residue was dissolved in diethyl ether, gaseous hydrogen chloride was passed through the resulting solution, the precipitate formed thereby was collected by suction filtration, and the semi-solid filter cake was stirred with a mixture of chloroform and an aqueous sodium carbonate solution. The organic phase was separated, dried with sodium sulfate, and the chloroform was distilled off, leaving 12.5 gm (69% of theory) of the title compound as a viscous yellow oil.

| Analysis: | C | H | N |
|---|---|---|---|
| Calculated: | 59.3% | 5.52% | 11.55% |

-continued

| Analysis: | C | H | N |
|---|---|---|---|
| Found: | 59.1% | 5.3% | 11.72%. |

The compounds of the formula I shown in Tables I–IV below were prepared by the following general procedures:

Starting compounds of the formula

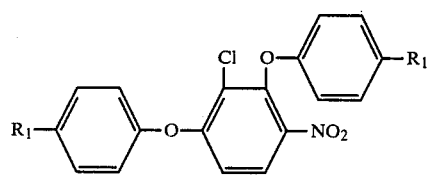

wherein $R_1$ is chlorine or hydrogen.

(a) Reaction with volatile amines:

Compound A was allowed to stand for 2 to 3 days with a 10% excess of the amine in dioxane. Thereafter, the reaction mixture was evaporated, the residue was taken up in diethyl ether, and the phenol formed thereby was removed by extraction with 2 N sodium hydroxide. The ether phase was extracted twice with water, dried with sodium sulfate and evaporated.

(b) Reaction with non-volatile amines:

Compound A was heated for 2 to 5 hours at 80° C. with a 10% excess of the amine in dioxane. Thereafter, the reaction mixture was evaporated, the residue was taken up in ether, and the resulting solution was extracted with 2 N sodium hydroxide. Residual amine starting material was removed by extraction with 2 N hydrochloric acid. The ether phase was then washed with water, dried with sodium sulfate and evaporated.

TABLE I

Compounds of the formula:

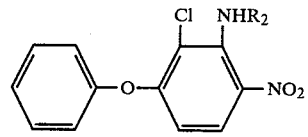

| Example No. | $R_2$ | Reaction conditions | Yield % of theory | RF-Values Acetone/heptane 1:1 | 27° C. Toluene | m.p. |
|---|---|---|---|---|---|---|
| 17 | CH$_3$— | 2 days RT* | 100% oil | | | 72–74° C. (from isopropanol) |
| 18 | C$_2$H$_5$— | 3 days RT* | 83.5% oil | 0.51 | 0.46 | |
| 19 | n-C$_3$H$_7$— | 2 hours 80° C. | 97.5% oil | 0.615 | 0.47 | |
| 20 | i-C$_3$H$_7$— | 6 hours 80° C. | 94% oil | 0.61 | 0.45 | |
| 21 | n-C$_4$H$_9$— | 2 hours 80° C. | 92% oil | 0.625 | 0.50 | |
| 22 | i-C$_4$H$_9$— | 5 hours 80° C. | 96.5% oil | 0.60 | 0.51 | |
| 23 | HO—CH$_2$—CH$_2$— | 2 hours 80° C. | 94% oil | 0.445 | 0.01 | |
| 24 | —CH(C$_2$H$_5$)$_2$ | 5 hours 80° C. | 93% oil | 0.47** | | |
| 25 | —CH$_2$—C≡CH | 5 hours 80° C. | 91% oil | 0.31 | | |

*RT = room temperature
**toluene/cyclohexane 1:1

TABLE II

Compounds of the formula:

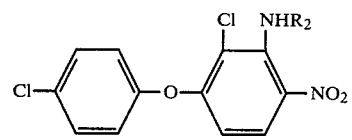

| Example No. | $R_2$ | Reaction Conditions | Yield % of theory | RF-Values Acetone/heptane 1:1 | 27° C. Toluene | m.p. |
|---|---|---|---|---|---|---|
| 26 | CH$_3$— | 2 days RT | 64 | | | 71–72° C. (from isopropanol) |
| 27 | CH$_2$=CH—CH$_2$ | 2 days RT | 98.5 | 0.52 | 0.51 | |
| 28 | —CH(C$_2$H$_5$)$_2$ | 3 days RT | 74 | | | |

TABLE III

Compounds of the formula:

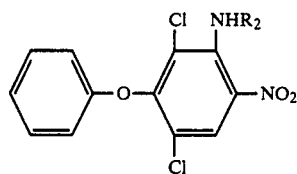

starting from 2,4-dichloro-6-nitro-1,3-diphenoxybenzene.

| Example No. | R2 | Amine/ Reaction Conditions | Yield % of theory | Properties/m.p. |
|---|---|---|---|---|
| 29 | CH3 | NH2CH3/24 hours at RT in dioxane | 74 | red crystals/101° C. |
| 30 | C2H5 | NH2C2H5/16 hours in dimethylsulfoxide | 85 | light brown oil, thin-layer chromatograph. uniform |
| 31 | i-C3H7 | NH2—i-C3H7/16 hours at RT in dixoane | 88 | orange crystals/83° C. |
| 32 | n-C4H9 | NH—n-C4H9/2 days at RT in dioxane | 92 | orange oil, thin-layer chromatograph. uniform |
| 33 | n-C12H25 | NH2—n-C12H25/5 days at RT in dioxane, purification by chromatography | 58 | orange crystals/43° C. |
| 34 | n-C18—H37 | NH2—n-C18H37/5 days at RT in dioxane, purification by chromatography | 51 | 47-48° C. |
| 35 | —CH2—CH2—OH | NH2CH2CH2OH/4 days at RT in dioxane | 100 | dark oil |
| 36 | —CH(C2H5)2 | NH2CH(C2H5)2/3 days at RT in dioxane | 63 | |

TABLE IV

Compounds of the formula

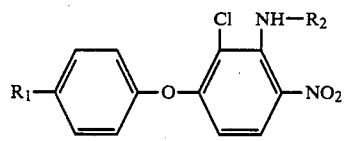

starting from compounds of the formula

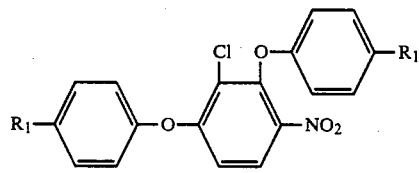

| Example No. | R1 | R2 | Reaction Conditions | Yield % of theory | RF-Values Acetone/ heptane 1:1 | 27° C. Toluene | m.p. |
|---|---|---|---|---|---|---|---|
| 37 | CH3 | CH3 | 2 days RT | 96 | 0.61 | 0.45 | |
| 38 | CH3 | CH2=CH–CH2— | 8 hours 60° C. | 94 | 0.63 | 0.515 | |
| 39 | F | C2H5 | 3 days RT | 93 | | | 69-70° C. (from isopropanol) |
| 40 | OCH3 | CH3 | 2 days RT | 89 | | | 100-101° C. |
| 41 | OCH3 | n-C3H7 | 3 hours 80° C. | 95 | 0.59 | 0.29 | |

As indicated above, the compounds embraced by formula I are very effective selective herbicides. More particularly, they are useful for pre-emergence and post-emergence weed control in agricultural fields, such as cereal grain, potato, corn, pea, barley and rice fields. Examples of weeds which can be controlled with the aid of the compounds of the formula I are wild mustard, amaranth, goosefoot, camomile, prickly grass, slender foxtail, yellow gallium and the like.

For example, the pre-emergence application of 2-chloro-3-phenoxy-6-nitro-N-(2-amino-ethyl)-aniline hydrochloride at the rate of 1 kg/hectar effectively controls the growth of wild mustard, amaranth, goosefoot, camomile, prickly grass and slender foxtail. Post-emergence application of the compound at the rate of 1 kg/hectar effectively controls the growth of yellow gallium, goosefoot and slender foxtail, and at a slightly higher rate also wild mustard, amaranth and camomile. The compatibility rate with respect to potatoes and corn is up to 3 kg/hectar, and with respect to wheat and peas it is more than 2.5 kg/hectar.

For herbicidal purposes the compounds of the formula I are incorporated as active ingredients into conventional herbicidal compositions, that is, compositions consisting essentially of an inert liquid or solid carrier and an effective herbicidal amount of the active ingredient, such as emulsion concentrates, wettable powders, granulates, dusting powders or the like. For example, the active ingredient content of emulsion concentrates or wettable powders, which are diluted with water prior to dissemination, is between about 10 and 95% by weight. In the case of dusting powders and granulates, which are disseminated without dilution, the active ingredient content may range from 0.2 to 20% by weight, preferably 0.5 to 3% by weight.

The following examples illustrate a few herbicidal compositions containing a compound of the formula I as the active ingredient and represent the best modes contamplated by of carrying out our invention.

EXAMPLE 42

Wettable powder

25% by weight 2-chloro-4-phenoxy-6-nitro-N-(2-amino-ethyl)-aniline hydrochloride
55% by weight kaolin
10% by weight colloidal silicic acid
9% by weight calcium lignin sulfonate
1% by weight sodium tetrapropylene-benzenesulfonate Prior to use, the powder is diluted with water to form a sprayable suspension containing about 0.05 to 0.5% by weight of the active ingredient.

EXAMPLE 43

Emulsion concentrate

20% by weight 2-chloro-4-phenoxy-6-nitro-N-(2-amino-ethyl)-aniline hydrochloride
70% by weight SHELLSOL A (mixture of liquid high-boiling-point aromatic hydrocarbon solvents)
6.5% by weight Tensiofix AS (emulsifier
3.7% by weight Tensiofix DS (emulsifier)

Prior to use, the concentrate is diluted with water to form a sprayable aqueous emulsion containing about 0.05 to 0.5% by weight of the active ingredient.

EXAMPLE 44

Dusting powder

1% by weight 2-chloro-3-phenoxy-6-nitro-N-[1-(methyl-carbamoyl)-ethyl]-aniline
98% by weight talcum
1% by weight methyl cellulose Any one of the other compounds embraced by formula I or an acid addition salt thereof may be substituted for the particular active ingredient in Examples 42 through 44, and the amount of active ingredient in these illustrative examples may be varied to achieve the effective range set forth above. Moreover, the amount and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing a compound of the formula

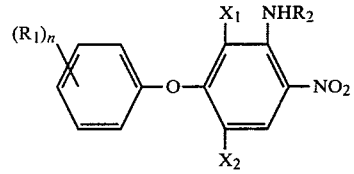

wherein
$R_1$ is hydrogen, halogen, alkyl of 1 to 8 carbon atoms, trifluoromethyl, —CN, acetyl, $C_1$-$C_4$-alkoxy or $C_1$-$C_4$-alkylthio;
n is 1 when $R_1$ has all the defined meanings, or 2 or 3 when $R_1$ is halogen or alkyl;
$R_2$ is hydrogen; alkyl of 1 to 18 carbon atoms; alkenyl of 2 to 16 carbon atoms; alkynyl of 2 to 16 carbon atoms; monosubstituted alkyl of 2 to 6 carbon atoms, where the substituent is hydroxyl, alkoxy of 1 to 4 carbon atoms, phenoxy, halo-phenoxy, (alkyl of 1 to 4 carbon atoms)phenoxy, (alkoxy of 1 to 4 carbon atoms) phenoxy, nitro-phenoxy, cyano-phenoxy, amino or (alkyl of 1 to 4 carbon atoms)thio; benzyl; halo-benzyl; trifluoromethyl-benzyl; —$NR_3R_4$; —$CHR_3$—$COOR_4$; or —$CHR_3$—$CONR_4R_5$;
where
$R_3$, $R_4$ and $R_5$ are each hydrogen or alkyl of 1 to 8 carbon atoms; and
$X_1$ and $X_2$ are each hydrogen or halogen,
which comprises reacting a compound of the formula

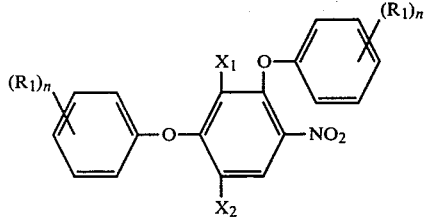

wherein n, $R_1$, $X_1$ and $X_2$ have the meanings previously defined, and the two

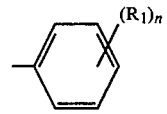

groups may be identical to or different from each other, with an amine of the formula $H_2N$—$R_2$ wherein $R_2$ has the meanings previously defined, at a temperature between about 20° and 160° C.

2. The method of claim 1, where the reaction is performed in an inert organic solvent or water.

* * * * *

UNITED STATES PATENT AND TRADEMARK OFFICE
CERTIFICATE OF CORRECTION

PATENT NO. : 4,364,875
DATED : December 21, 1982
INVENTOR(S) : RICHARD SEHRING ET AL.

It is certified that error appears in the above-identified patent and that said Letters Patent is hereby corrected as shown below:

Column 4, line 63; Column 5, line 44:
"phenox-" should read -- phenoxy)- --

Column 4, line 64; Column 5, line 45: Delete "y)"

Signed and Sealed this

Twelfth Day of July 1983

[SEAL]

Attest:

GERALD J. MOSSINGHOFF

Attesting Officer

Commissioner of Patents and Trademarks